(12) United States Patent
Tirapu Azpiroz et al.

(10) Patent No.: US 11,618,032 B2
(45) Date of Patent: Apr. 4, 2023

(54) MULTIPLEXED TESTING STRIP DEVICE

(71) Applicant: INTERNATIONAL BUSINESS MACHINES CORPORATION, Armonk, NY (US)

(72) Inventors: Jaione Tirapu Azpiroz, Rio de Janeiro (BR); Matheus Esteves Ferreira, Rio de Janeiro (BR); Ademir Ferreira da Silva, São Paulo (BR); Daniel Vitor Lopes Marcondes Marçal, São Paulo (BR); Ricardo Luis Ohta, São Paulo (BR); Mathias B. Steiner, Rio de Janeiro (BR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 274 days.

(21) Appl. No.: 17/008,621

(22) Filed: Aug. 31, 2020

(65) Prior Publication Data

US 2022/0062911 A1 Mar. 3, 2022

(51) Int. Cl.
*B01L 9/00* (2006.01)
*G01N 21/78* (2006.01)
(Continued)

(52) U.S. Cl.
CPC ............. *B01L 9/52* (2013.01); *G01N 11/00* (2013.01); *G01N 21/78* (2013.01); *G01N 27/028* (2013.01);
(Continued)

(58) Field of Classification Search
CPC .. B01L 9/52; B01L 2200/025; B01L 2200/12; B01L 2300/021; B01L 2300/027;
(Continued)

(56) References Cited

U.S. PATENT DOCUMENTS 5,441,896 A 8/1995 Noppe et al.
5,459,078 A * 10/1995 Kline ................. G01N 33/9453
436/538
(Continued)

FOREIGN PATENT DOCUMENTS

CN 1672053 A 9/2005
CN 1653323 A 10/2005
(Continued)

OTHER PUBLICATIONS

International Search Report and Written Opinion dated Sep. 28, 2021 in related application No. PCT/CN2021/104510; 12 pgs.

*Primary Examiner* — Jennifer Wecker
*Assistant Examiner* — Alea N. Martin
(74) *Attorney, Agent, or Firm* — Intelletek Law Group, PLLC; Gabriel Daniel, Esq.

(57) ABSTRACT

A multiplexed testing strip testing device includes a hydrophobic paper-based strip housing element configured for placement of one or more testing strips. One or more alignment markers on the hydrophobic paper-based housing element are marked to facilitate placement of the one or more testing strips. A cover element is arranged above the strip housing element and includes a machine-readable test identifier on an upper surface. A removably attached filtering element is arranged on the hydrophobic paper-based strip housing element.

20 Claims, 9 Drawing Sheets

US 11,618,032 B2
Page 2

(51) Int. Cl.
*G01N 27/02* (2006.01)
*G01N 11/00* (2006.01)

(52) U.S. Cl.
CPC ..... *B01L 2200/025* (2013.01); *B01L 2200/12* (2013.01); *B01L 2300/021* (2013.01); *B01L 2300/027* (2013.01); *B01L 2300/041* (2013.01); *B01L 2300/0681* (2013.01); *B01L 2300/0861* (2013.01); *B01L 2300/126* (2013.01); *B01L 2300/161* (2013.01)

(58) Field of Classification Search
CPC ....... B01L 2300/041; B01L 2300/0681; B01L 2300/0861; B01L 2300/126; B01L 2300/161; G01N 11/00; G01N 21/78; G01N 27/028
See application file for complete search history.

(56) References Cited

U.S. PATENT DOCUMENTS

| | | | |
|---|---|---|---|
| 6,844,149 B2 | 1/2005 | Goldman | |
| 7,393,697 B2 | 7/2008 | Charlton | |
| 8,663,909 B2 | 3/2014 | Gazenko | |
| 2004/0214347 A1 | 10/2004 | LaBorde et al. | |
| 2007/0287198 A1 | 12/2007 | LaBorde et al. | |
| 2014/0295415 A1* | 10/2014 | Rolland | C12Q 1/68 435/6.1 |
| 2016/0051980 A1* | 2/2016 | Hong | G01N 33/558 506/39 |
| 2016/0274105 A1* | 9/2016 | Whitesides | G01N 33/54386 |
| 2017/0234858 A1 | 8/2017 | Depa et al. | |
| 2019/0118175 A1 | 4/2019 | Kim et al. | |
| 2019/0302097 A1 | 10/2019 | Niu et al. | |
| 2020/0064343 A1 | 2/2020 | Bell | |
| 2020/0378957 A1* | 12/2020 | Azpiroz | G01N 33/558 |

FOREIGN PATENT DOCUMENTS

| | | | |
|---|---|---|---|
| CN | 100342233 C | 10/2007 | |
| CN | 101467042 A | 6/2009 | |
| CN | 202631544 U | 12/2012 | |
| CN | 102221547 B | 8/2013 | |
| CN | 106442511 A | 2/2017 | |
| CN | 108712877 A | 10/2018 | |
| CN | 106053456 B | 11/2018 | |
| WO | WO-2019025630 A1 * | 2/2019 | ............ B01L 3/5023 |

* cited by examiner

MULTIPLEXED TESTING STRIP DEVICE

BACKGROUND

Technical Field

The present disclosure generally relates to testing devices using paper testing strips for extracting chemical information from liquid samples, and more particularly, to multiplexing chemical testing strips.

Description of the Related Art

Today, there are increased efforts being made to monitor environmental conditions in a variety of agricultural and manufacturing settings. Unlike lateral flow immunoassays (e.g., dengue tests) that have a binary response indicating a presence or absence of a target antibody, paper-based chemical testing strips (e.g., dipstick tests) have become popular as they can exhibit a ranged colorimetric response to a chemical reaction, providing additional information. The ability to test for a concentration of a chemical in a sample, and a fast test result based on the shade of a color on the paper-based testing strip, contribute to the popularity of this form of testing.

However, the use of paper testing strips has some disadvantages. The immersion of a paper testing strip in samples, such as soil or wastewater, tends to increase the possibility that debris can adversely affect the results. For example, the shade of the colorimetric strip may be adversely impacted and the reading may be inaccurate. Also, the handling of testing strips with bare hands can increase the chances of cross-contamination, especially if several different testing strips are necessary to execute different analysis.

SUMMARY

According to various embodiments, a multiplexed chemical testing strip device includes a hydrophobic paper-based strip housing element configured for placement of one or more testing strips. One or more alignment markers are positioned on the hydrophobic paper-based housing element to facilitate placement of the one or more testing strips. A cover element is arranged above the strip housing element and including a machine-readable test identifier on an upper surface, and a removably attached filtering element is arranged on the hydrophobic paper-based strip housing element. The removably attached filtering element provides a cleaner sample, and its removal facilitates a more accurate colorimetric reading.

In an embodiment, a color reference information area is arranged on an upper surface of the cover element for result interpretation and digitalization by a digital Information Technology (IT) system. The one or more testing strips received by the hydrophobic paper-based strip housing element display colorimetric results, and at least one of the machine-readable test identifier or the color reference information area identifies the test being performed. Conventional devices do not perform multiple tests on the same sample and do not provide test identification.

In an embodiment, the testing strips are a plurality of testing strips, and the hydrophobic paper-based strip housing element is configured to secure the plurality of the testing strips for simultaneous immersion in a sample for multiplex testing of the sample.

In an embodiment, at least some of the plurality of testing strips secured by the hydrophobic paper-based strip housing element are configured to perform different chemical testing of the sample, respectively.

In an embodiment, the hydrophobic paper-based strip housing element includes a plurality of channels formed by the strip housing element and extends in a longitudinal direction. Each respective channel of the plurality of channels has a length and a width configured to receive one testing strip of the one or more testing strips.

In an embodiment, the hydrophobic paper-based strip housing element includes a plurality of grooves extending in a longitudinal direction. Each respective groove of the plurality of grooves has a length and a width configured to receive one testing strip of the one or more testing strips.

In an embodiment, the removably attached filtering element is adhered to the upper surface of the cover element and the filtering element is configured to filter a turbid sample.

In an embodiment, the removably attached filtering element is configured to filter samples including particulates of the liquid sample, soil, or wastewater. This filtering can remove contaminates that can change a shade of the colorimetric testing strips, thereby enhancing the accuracy of the result.

In an embodiment, the removably attached filtering element comprises a peelable filtering element including a filtering paper portion and a peelable portion arranged along part of a periphery of the filtering paper portion. The filtering element removes particulates from the sample, and the peelable portion facilitates a more accurate test result, as the image of the colorimetric testing strips are captured for processing, and removal of the peelable portion reduces distortion of the image.

In an embodiment, the peelable filtering element is configured to be removed from the test device by peeling to enhance viewing of the testing strips for result determination and digitalization.

In an embodiment, the one or more testing strips received by the hydrophobic paper-based strip housing element display colorimetric results. The testing strip device further includes a timer element configured to indicate a predetermined time period at which a testing of the input sample is complete.

In an embodiment, the timer element is a paper-based hydrophilic timing channel formed by hydrophobic material. The timer element provides a colorimetric display when a predetermined period of testing time for a test being performed by one of the testing strips has elapsed.

In an embodiment, the predetermined period of time at which the timer element visually indicates that a testing time has elapsed is configured based on one or more of the viscosity of the sample being tested, an impedance of the paper path, or the test performed by the testing strips.

In an embodiment, the cover element comprises a top cover having a transparent portion configured to view test results of the one or more testing strips, and to facilitate an image capture or visualization of the testing strips for result interpretation and digitalization.

In another embodiment, a method of manufacturing a multiplexed chemical testing strip device includes providing a hydrophobic paper-based strip housing element configured to receive one or more testing strips for testing a sample. The hydrophobic paper-based housing element is marked with one or more alignment markers for the arrangement of the testing strips. A cover element is arranged above the strip housing element and includes a machine-readable test identifier on its upper surface. A removably attached filtering element is arranged on the hydrophobic paper-based strip housing element.

In an embodiment, the strips are provided with a color reference information area on an upper surface of the cover element for result interpretation and digitalization by a digital Information Technology (IT) system. At least one of the machine-readable test identifier or the color reference information identifies the test being performed.

In an embodiment, testing strips received by the hydrophobic paper-based strip housing element are colorimetric testing strips, and the hydrophobic paper-based strip housing element is configured to secure the plurality of the testing strips for simultaneous immersion in a sample for multiplex testing of the sample.

In an embodiment, the removably attached filtering element is configured for filtering a turbid sample by adhering the removably attached filtering element to the cover element along a periphery to be peelable from the multiplexed chemical testing strip device after performing a filtering operation of the turbid sample.

According to an embodiment, a multiplexed chemical testing strip device includes a hydrophobic paper-based strip housing element configured to receive a plurality of colorimetric testing strips. One or more alignment markers are arranged on the hydrophobic paper-based housing element for placement of the plurality of colorimetric testing strips. A cover element is arranged above the strip housing element and includes a machine-readable test identifier comprising a Barcode, a Quick Response (QR) code, or a Radio-Frequency Identification (RFID) on an upper surface. A removably attached filtering element is arranged on the hydrophobic paper-based strip housing element, and a color reference information area on an upper surface of the cover element is provided for result interpretation and digitalization by a digital Information Technology (IT) system. At least one of the machine-readable test identifier or the color reference information identifies the test being performed.

In an embodiment, the plurality of testing strips received by the hydrophobic paper-based strip housing element, display colorimetric results. At least some of the plurality of testing strips secured by the hydrophobic paper-based strip housing element are configured to perform different chemical testing of the sample, respectively.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all the components or steps that are illustrated. When the same numeral appears in different drawings, it refers to the same or like components or steps.

DETAILED DESCRIPTION

Overview

In the following detailed description, numerous specific details are set forth by way of examples to provide a thorough understanding of the relevant teachings. However, it should be apparent that the present teachings may be practiced without such details. In other instances, well-known methods, procedures, components, and/or circuitry have been described at a relatively high-level, without detail, to avoid unnecessarily obscuring aspects of the present teachings.

The multiplexed testing strip device according to the present disclosure overcomes many shortcomings of known chemical testing devices and methods. A removably attached filtering element can prevent inaccurate results, particularly in a liquid sample with debris such as a soil extract or wastewater. The turbidity of a sample can be prevented from affecting the shading of colorimetric testing strips by removal of the filtering element subsequent to at least partial immersion of the testing device in a sample. The removal of the filtering element permits a clearer image of the testing strips to be captured for image processing, test result interpretation and digitalization. Conventional methods where large color scale cards are used, suffer from frequent shadow and illumination errors, and lack an identification of a test performed by the testing strips. These problems are addressed by the addition of colorimetric references and image processing markers that allow the information to be accurately processed by an IT system.

The multiplexed testing strip device is applicable in a very wide field of applications, including but not in any way limited to soil sample testing, medical testing (e.g. urine, blood and/or other bodily fluids) food safety testing (e.g. milk safety testing for adulterants, contaminants, bacteria and/or alcohol traces), agriculture and/or livestock operations.

Reference now is made in detail to the examples illustrated in the accompanying drawings and discussed below.

Example Architecture

Figure 1:
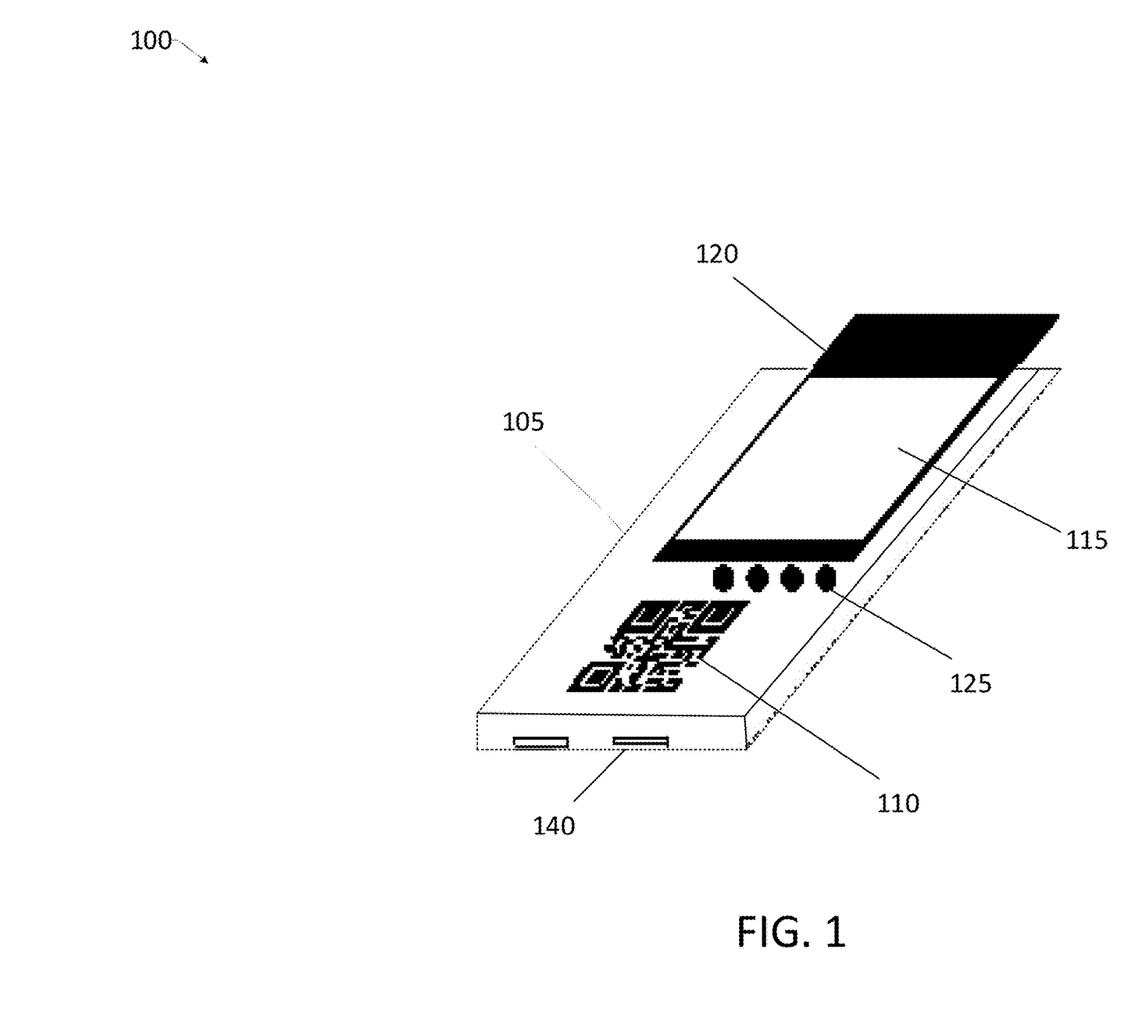
FIG. 1 is a perspective view of a multiplexed testing strip device, consistent with an illustrative embodiment.

FIG. 1 is a perspective view of a multiplexed testing strip device 100, consistent with an illustrative embodiment. It is to be understood that the rapid testing device shown is provided for illustrative purposes, and the present disclosure is not limited to the illustration shown and described.

With continued reference to FIG. 1, the multiplexed testing strip device 100 includes a cover element 105, a machine-readable test identifier 110, a removably attachable filtering element 115 including a carrier 120, a color reference 125, and testing strips 140. The cover element is constructed of a paper board, and may be made of or coated with a hydrophobic material.

The machine-readable test identifier 110 is shown in the form of a Quick Response (QR) code, however, any other type of machine-readable test identifier can be used. The QR code is configured to uniquely identify the tests performed by the testing strips, but alternatively, or in addition thereto, may also provide information regarding the expiration date of the testing strips, the manufacturer of the testing strips and/or the multiplexed strip testing device, etc.

The removably attached filtering element 115 is arranged typically over an opening in the cover element 105 to protect the testing strips from excessive debris and contaminants that may not be the subject of the test. For example, when testing a soil sample, the soil may have debris, such as small pieces of leaves, twigs, stones, etc., that can cause a turbidity of the sample that may adversely impact the colorimetric results of the testing strips 140. After at least partial submersion of immersion of the multiplexed testing strip device, and removal of the testing strip device from the sample, the filtering element 115 may be removed from the testing device by peeling or pulling the carrier 120. In this illustrative embodiment, the carrier extends from the end of the testing device. By removing the filtering element, the observance of the colorimetric testing strips is greatly enhanced, thereby providing another enhancement in more accurate test results in addition to the debris removal.

Figure 2:
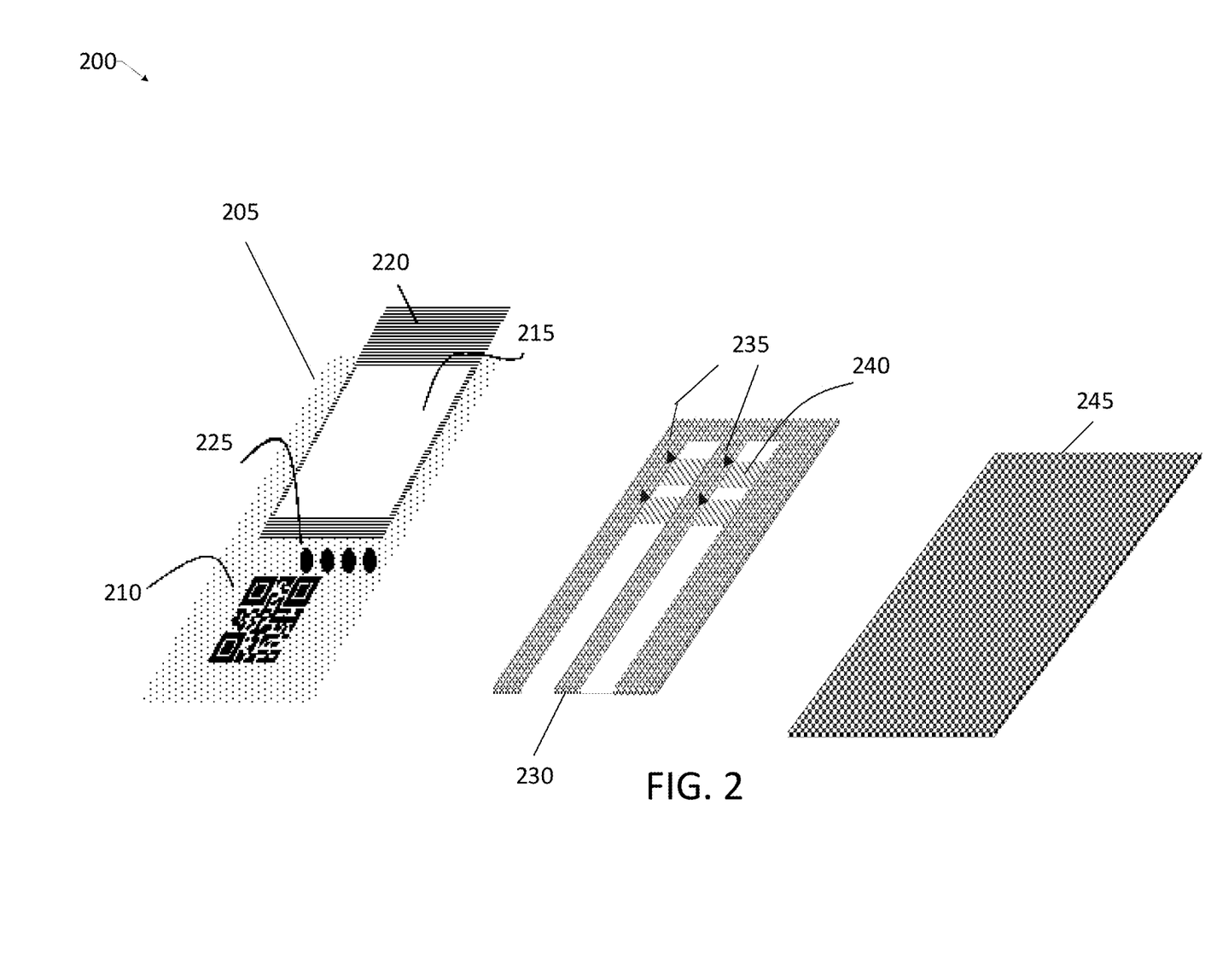
FIG. 2 is an illustration in an exploded view of the multiplexed testing strip device, consistent with an illustrative embodiment.

FIG. 2 is an illustration in an exploded view of the multiplexed testing strip device, consistent with an illustrative embodiment. FIG. 2 shows the cover element 205, a hydrophobic paper-based housing element 230, and a bottom cover 245. Similar to FIG. 1, the cover element 205 in FIG. 2 has a removably attached filtering element 215 with a carrier 220 arranged on an upper surface of the cover element. The machine-readable test identifier 210 and the color reference 225 are also included.

The hydrophobic paper-based housing element 230 includes alignment markers 235 and testing strips 240. The housing element 230 in this illustrative embodiment defines two channels configured for the arrangement of the testing strips 240 shown. Alignment markers 235 are provided to assist in the arrangement of the testing strips 240 in the housing element 230, and in an embodiment may be protrusions that assist in securing the testing strips in place. The bottom cover 245 can be constructed of a glossy paper material, that along with the cover element 205, may form a cover unit that protects the housing element 230, and the testing strips 240.

Figure 3A:
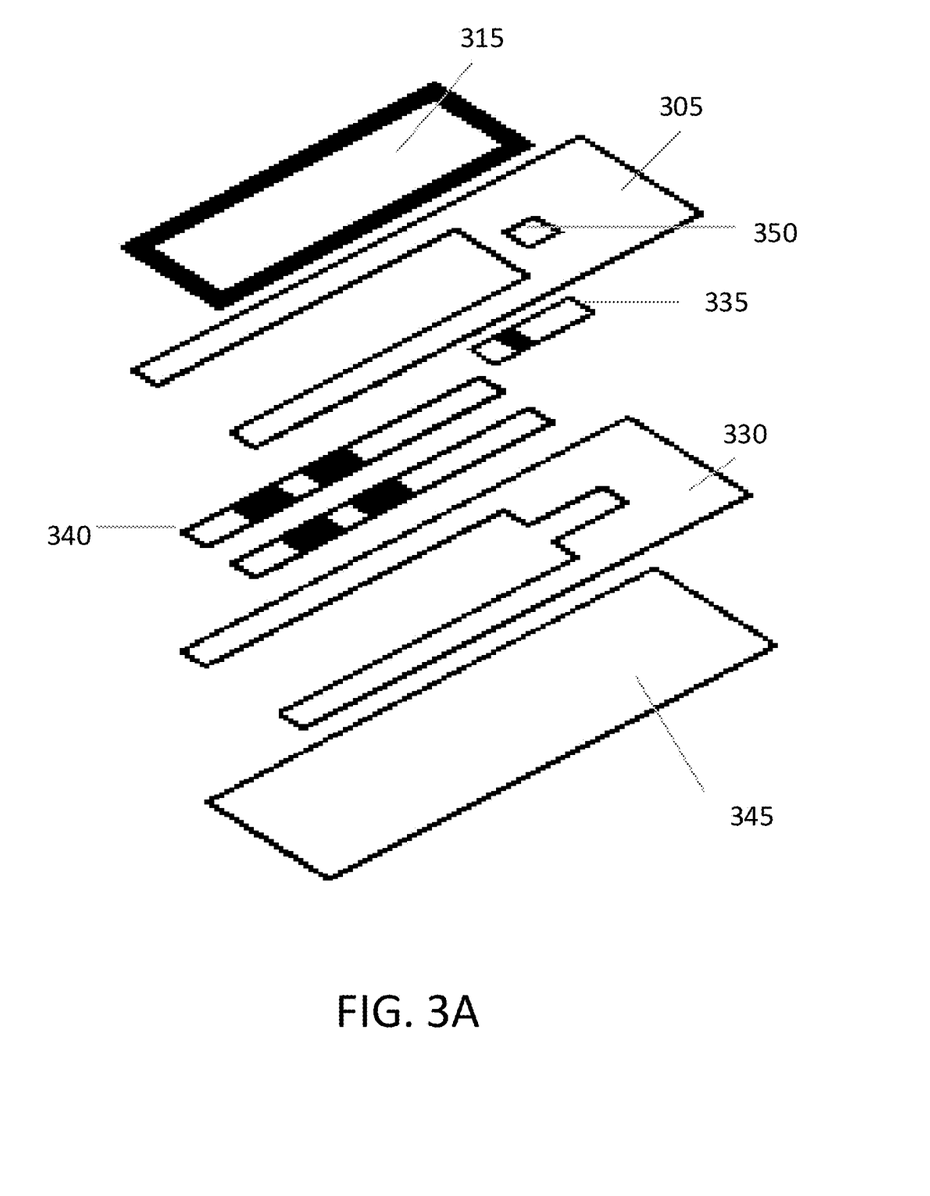
FIGS. 3A and 3B illustrate a multiplexed testing strip device, consistent with an illustrative embodiment.
Figure 3B:
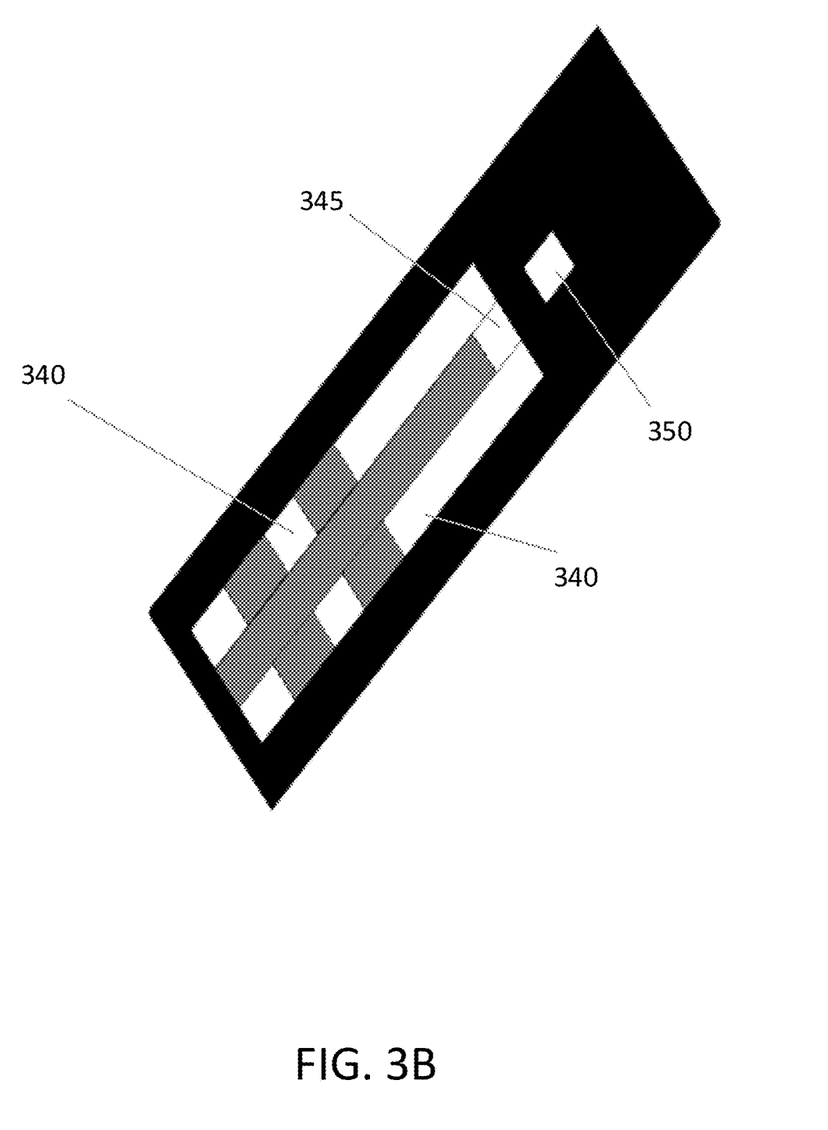

FIGS. 3A and 3B illustrate a multiplexed testing strip device, consistent with an illustrative embodiment. FIG. 3A is an exploded view including a removably attached filtering element 315, cover element 305, strip housing element 330, and bottom cover 345. Strips 340 and 335 are shown.

The removably attached filtering element 315 is arranged over the opening in the top cover 305. In this embodiment, the cover 305 has an additional window 350, and it can be seen that the housing element 330 has an additional channel that can receive the testing strip 335, whereas the strips 340 are arranged in the wider opening of the housing element. While the test 340 may be testing for different chemicals, the additional strip 335 may be a timer strip. The timer strip may be used to indicate that the other testing strips 340 are ready for analysis. Alternatively, the testing strip 335 may be used as an integrity check of the turbidity of the sample, a distribution strip, an additional filtering step, and an indication that of turbidity may require adjustment of the determination result of the other testing strips.

FIG. 3B shows the multiplexed strip testing device in an assembled view, with testing strips 340, and the testing strip 335 visible via the window 350.

Figure 4:
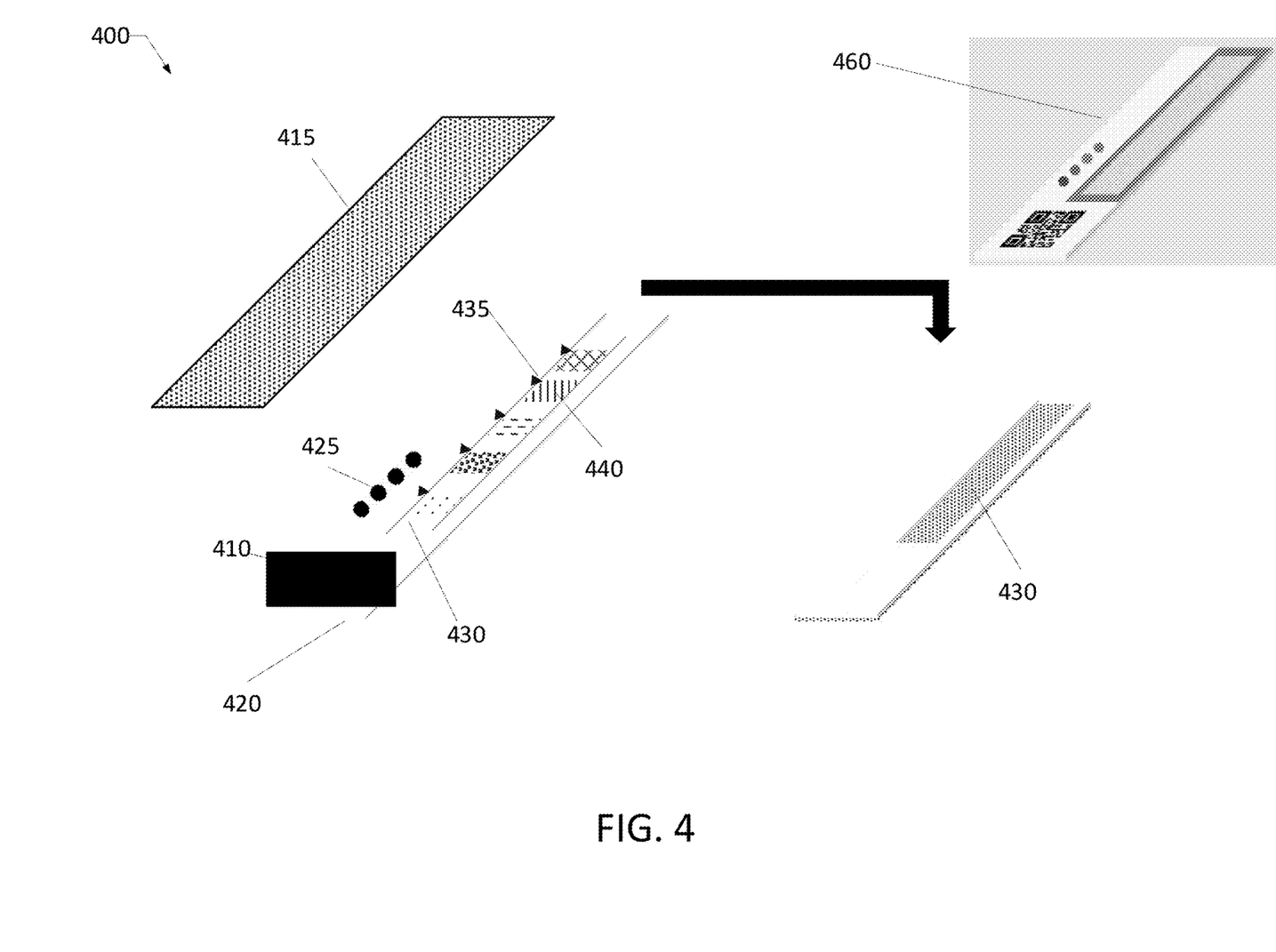
FIG. 4 illustrates a multiplexed testing strip device having an alignment grove, consistent with an illustrative embodiment.

FIG. 4 illustrates a multiplexed testing strip device 400 having an alignment grove, consistent with an illustrative embodiment. The multiplexed strip testing device 400 includes a peel-off filtering element 415 constructed of filtering paper and an adhesive. The filtering paper can also serve as a top cover. A bottom cover 420 includes the machine test identifier 410, color reference 425, alignment markers 435, and testing strip 440, all of which function as previously discussed hereinabove. In this illustrative embodiment, a groove 430 may be embossed or etched in the bottom cover, and sized to receive the testing strip 440. The device is shown after assembly 460. In this illustrative embodiment, there are fewer components, and as the testing device is disposable, there is less waste. The multiplexed testing strip device shown in FIG. 4 has one groove for illustrative purposes, but multiple grooves can be made in the bottom cover 420 to conduct simultaneous testing for various chemicals by the partial immersion of a single testing device in a sample.

Figures 5A, 5B, 5C:
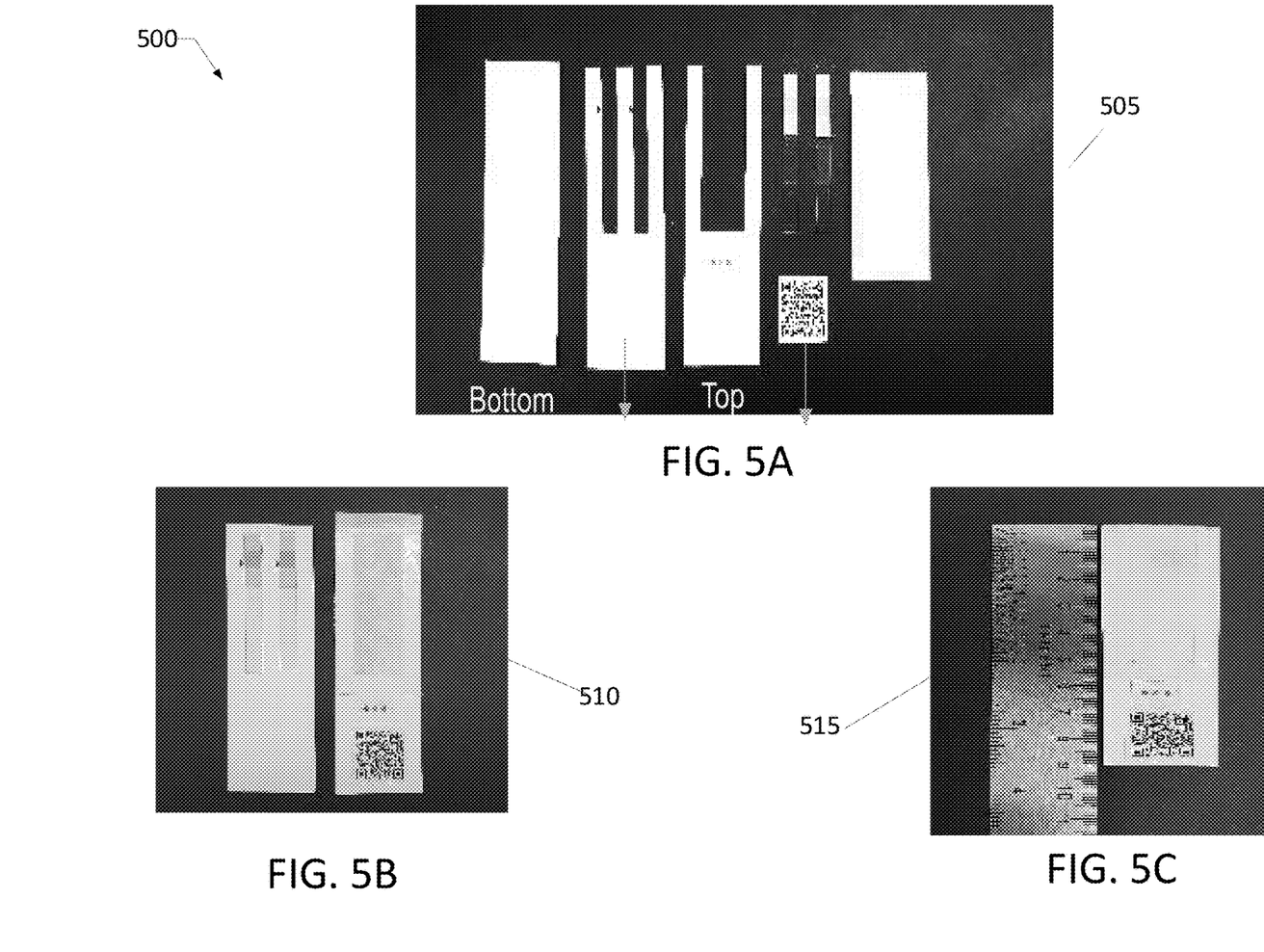
FIGS. 5A, 5B, and 5C illustrate a prototype implementation of a multiplexed testing strip device, consistent with an illustrative embodiment.

FIGS. 5A, 5B, and 5C illustrate a prototype implementation 500 of a multiplexed testing strip device, consistent with an illustrative embodiment. In FIG. 5A, an image 505 of the various components are shown unassembled. As illustrated, there is a bottom, a housing element, a top, a filtering element, and testing strips with a machine-readable test identifier.

FIG. 5B shows an image 510 of the multiplexed testing strip device in a partial state of assembly. In FIG. 5C, a final assembled image 515 is shown alongside a ruler to illustrate the compactness of the device.

Figure 6:
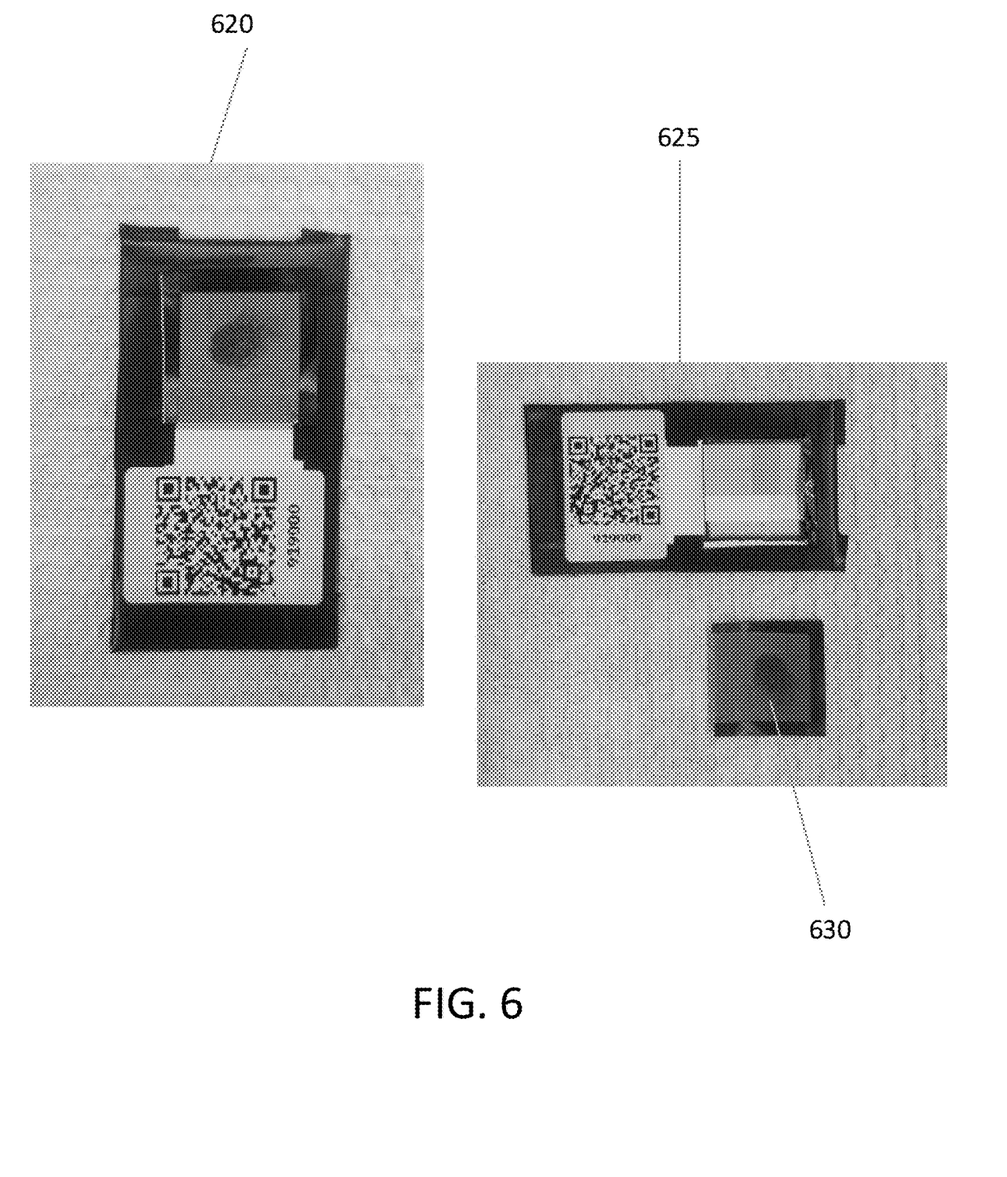
FIG. 6 illustrates a prototype of the multiplexed testing strip device, consistent with an illustrative embodiment.

FIG. 6 illustrates a prototype of the multiplexed testing strip device, consistent with an illustrative embodiment. As shown at 620 the removable filtering element is attached, and at 625, the removable filtering element 630 has been removed to facilitate image processing of the colorimetric testing strips.

Figure 7:
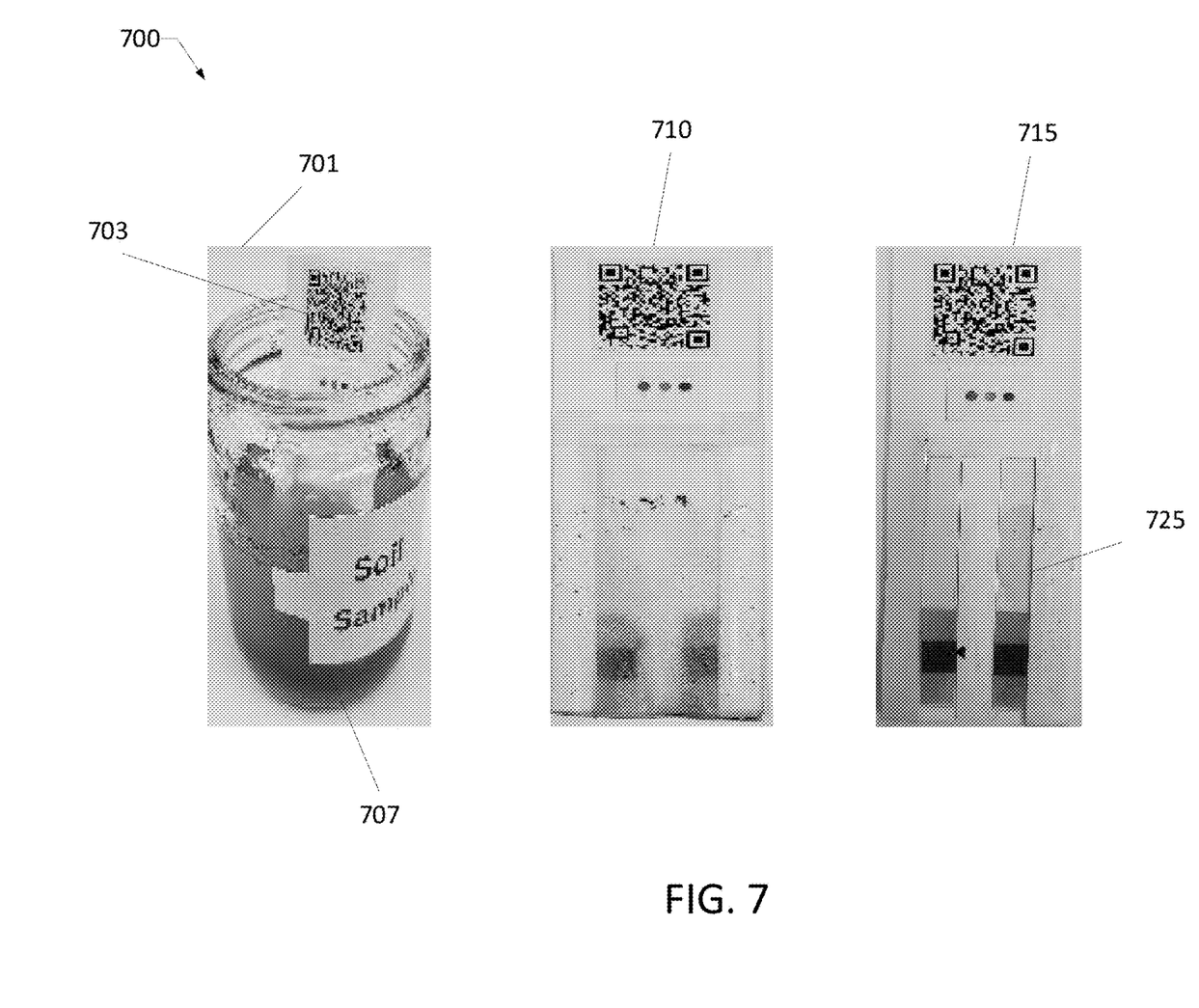
FIG. 7 illustrates the multiplexed testing strip device in operation, testing a soil sample, consistent with an illustrative embodiment.

FIG. 7 illustrates the multiplexed testing strip device in operation 700 testing a soil sample, consistent with an illustrative embodiment. At 701, the testing device 703 is arranged in the soil sample 707. At 710, the testing device is shown after removal from the soil sample, and at 715, the device is shown after removal of the filtering element. It can be seen the difference in clarity of the testing strips 725 after removal of the filter element. The filtering element both protects the integrity of the colorimetric strips, and the removal enhances the accuracy of the test results.

Example Processes

Figure 8:
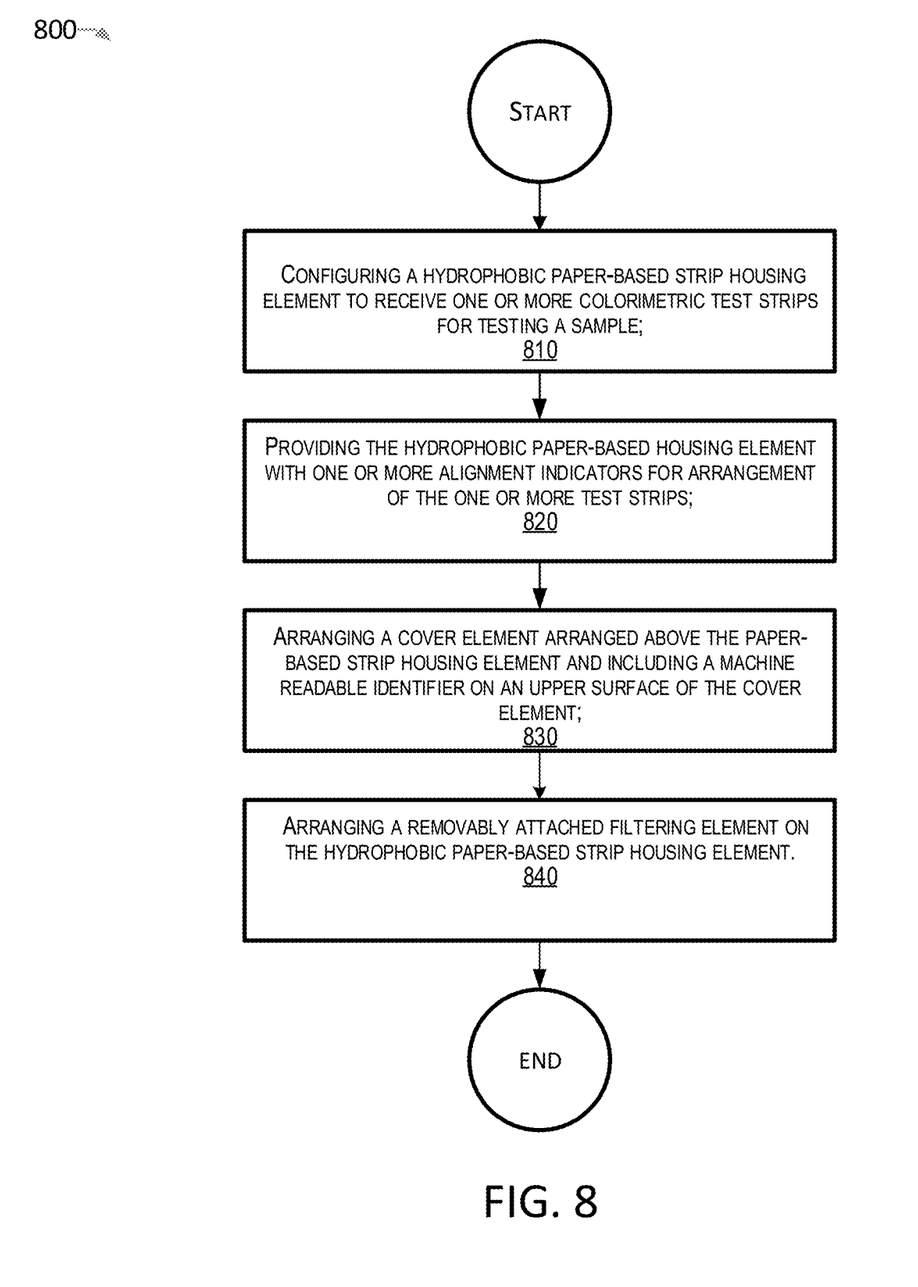
FIG. 8 is a flowchart illustrating a method of manufacturing a multiplexed testing strip device, consistent with an illustrative embodiment.

With the foregoing overview of the example architecture, it may be helpful now to consider a high-level discussion of an example process. To that end, FIG. 8 is a flowchart 800 of a manufacturing process of a multiplexed testing device shown in FIGS. 1, 2, and 3. It is to be understood that the order of the operations of the flowchart of FIG. 8 is provided for illustrative purposes, and the manufacturing operations can be performed in a different order than shown in FIG. 8.

With reference to the flowchart in FIG. 8, at operation 810, a hydrophobic paper-based strip housing element is configured for placement of one or more testing strips. The strip housing element 230 such as shown in FIG. 2, or the housing element 430 (FIG. 4) having one or more embossed grooves 430, are two of such non-limiting housing arrangements that are within the scope of the multiplexed testing device according to the present disclosure. The testing strips, for example, can be colorimetric testing strips 240, 340, 345 such as shown in FIG. 2 and FIG. 3B. However, the multiplexed testing device of the present disclosure is not limited to commercially available colorimetric testing strips, and other types of testing strips, including custom-designed testing strips with one or more hydrophilic channels can be arranged within the paper-based housing strip housing element.

At operation 820, the hydrophobic paper-based housing element with one or more alignment markers (e.g. Alignment indicators) for arrangement of the one or more testing strips is provided. Alignment markers 235, 435 (FIGS. 2 and 4) are non-limiting examples of alignment markers that may be realized as visual guides and/or as protrusions that prevent the testing strips from movement within the housing element.

At operation 830, a cover element is arranged above the strip housing element. The cover element may include a machine-readable test identifier on an upper surface of the cover element. For example, FIGS. 1 and 2 show cover elements 105, 205 with respective QR codes 110, 210. The QR code may provide various information that may include, but is not limited to, a unique test identification (ID) for tracking purposes, a manufacturing information, an expiration date of the testing device, testing strip types, number of strip tests, etc. Bar codes or any other type of machine-readable test identifier (e.g. magnetic coding, Radio-frequency Identification—RFID) can be used. The cover element 205 may form a cover unit in conjunction with a bottom cover element 245 (FIG. 2). The bottom cover 245 in this illustrative embodiment is constructed of a glossy coated paper or any paper/cardboard with protective coating to prevent liquid sipping. The cover element may also be marked with alignment and/or colorimetric references 225 (FIG. 2). The colorimetric references 225 can be realized as different color dots provided as a reference for an imaging processing device to determine/estimate a test result of the colorimetric testing strips. For example, after the multiplexed testing device is at least partially immersed in a sample and then removed and a predetermined time period has passed, an image of the colorimetric testing strips may be captured by a camera of a smartphone or other device for analysis. As the multiplexed testing device may test samples in either indoor or outdoor environments, the ambient lighting may be different and the colorimetric references can serve as a guide for the image processing to adjust the obtained image of the test results to enhance the accuracy of the testing.

At operation 840, a removably attached filtering element is arranged on the hydrophobic paper-based strip housing element. FIG. 1 shows a filtering paper 115 and a carrier 120 for attaching or removing the paper element. For example, the carrier may have an adhesive on one side for attachment to the cover element, and the carrier 120 can be manually, or with a tool, peeled away from the cover element 105, 205 (FIGS. 1 and 2). As the filtering paper 115 is attached to the carrier 120, the entire filtering element can be removed from the cover element 105, 205. One of the benefits of a removably attached filtering element is that while debris in the sample may be prevented from adversely impacting the colorimetric testing strips, the removal of the filtering element provides for a more accurate reading after the at least partial immersion of the multiplexed testing device into a sample. FIG. 7 shows an image 701 of a multiplexed testing device 703 immersed in a soil sample 707, followed by the captured image 710 of the multiplexed testing device with the filtering element attached, and the captured image 715 of the multiplexed testing device after the removably attached filtering element is separated (e.g., peeled or removed) from the multiplexed device. The view of the testing strips 725 is enhanced in clarity by removal of the filtering element. Accordingly, an image processing device that analyzes the image of the multiplexed testing device will provide a more accurate test result, particularly in cases where there is turbidity in the sample.

Although the basic method of manufacturing ends at operation 840, there can be additional operations such as including a timer element, to take into account eventual reaction time to obtain the colorimetric reactions.

CONCLUSION

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments have more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A multiplexed chemical testing strip device, comprising:
    a hydrophobic paper-based strip housing element configured for placement of one or more testing strips;
    one or more alignment markers positioned on the hydrophobic paper-based housing element configured to facilitate placement of the one or more testing strips;
    a cover element arranged above the strip housing element and including a machine-readable test identifier on an upper surface; and
    a removably attached filtering element configured to remove contaminates that can change a shade of the one or more testing strips and arranged on the hydrophobic paper-based strip housing element to reduce a distortion of an image of the one or more testing strips.

2. The testing strip device according to claim 1, further comprising a color reference information area arranged on an upper surface of the cover element for result interpretation and digitalization by a digital Information Technology (IT) system, wherein:
    the one or more testing strips received by the hydrophobic paper-based strip housing element display colorimetric results, and
    at least one of the machine-readable test identifier or the color reference information identifies the test being performed.

3. The testing strip device according to claim 2, wherein:
    the one or more testing strips comprise a plurality of testing strips, and
    the hydrophobic paper-based strip housing element is configured to secure the plurality of the testing strips for simultaneous immersion in a sample for multiplexed testing of the sample.

4. The testing strip device according to claim 3, wherein at least some of the plurality of testing strips secured by the hydrophobic paper-based strip housing element are configured to perform different chemical testing of the sample, respectively.

5. The testing strip device according to claim 1, wherein:
    the hydrophobic paper-based strip housing element comprises a plurality of channels formed by the strip housing element and extends in a longitudinal direction, and
    each respective channel of the plurality of channels has a length and a width configured to receive one testing strip of the one or more testing strips.

6. The testing strip device according to claim 1, wherein:
    the hydrophobic paper-based strip housing element comprises a plurality of grooves extending in a longitudinal direction, and
    each respective groove of the plurality of grooves has a length and a width configured to receive one testing strip of the one or more testing strips.

7. The testing strip device according to claim 1, wherein:
    the removably attached filtering element is adhered to the upper surface of the cover element, and
    the filtering element is configured to filter the sample.

8. The testing strip device according to claim 7, wherein the removably attached filtering element is configured to filter samples comprising at least one of particulates of the liquid sample, soil, or wastewater.

9. The testing strip device according to claim 1, wherein the removably attached filtering element comprises a peelable filtering element comprising a filtering paper portion and a carrier portion arranged along part of a periphery of the filtering paper portion.

10. The testing strip device according to claim 8, wherein the carrier portion is configured to peelably remove the filtering element from the test device to enhance viewing of the testing strips to facilitate a result determination and a digitalization of the sample tested.

11. The testing strip device according to claim 1, wherein the one or more testing strips received by the hydrophobic paper-based strip housing element display colorimetric results, and the testing strip device further comprises a timer element configured to indicate a predetermined time period at which a testing of the input sample is complete.

12. The testing strip device according to claim 11, wherein the timer element comprises a paper-based hydrophilic timing channel formed by a hydrophobic material, wherein the timer element provides a colorimetric display when a predetermined period of testing time for a test being performed by one or more of the testing strips has elapsed from a contact of the sample with the timer element.

13. The testing strip device according to claim 12, wherein the predetermined period of time at which the timer element visually indicates that a testing time has elapsed is configured based on one or more of the viscosity of the sample being tested, an impedance of the paper path, and the test performed by the testing strips.

14. The testing strip device according to claim 1, wherein the cover element comprises a top cover having a transparent portion configured to view test results of the one or more testing strips and to facilitate an image capture or a visualization of the one or more testing strips for result interpretation and digitalization.

15. A method of manufacturing a multiplexed chemical testing strip device, comprising:

configuring a hydrophobic paper-based strip housing element configured to receive one or more testing strips for testing a sample;

providing the strip housing element with one or more alignment markers for arrangement of the one or more testing strips;

arranging a cover element above the strip housing element and including a machine-readable test identifier on an upper surface of the cover element; and arranging a removably attached filtering element configured to remove contaminates that can change a shade of the one or more testing strips on the strip housing element to reduce a distortion of an image of the one or more testing strips.

16. The method according to claim 15, further comprising providing a color reference information area on an upper surface of the cover element for result interpretation and digitalization by a digital Information Technology (IT) system, wherein at least one of the machine-readable test identifier or the color reference information, identifies the test being performed.

17. The method according to claim 16, wherein the one or more testing strips comprise a plurality of colorimetric testing strips, and the method further comprises configuring the hydrophobic paper-based strip housing element to secure the colorimetric testing strips for simultaneous immersion in a sample for multiplex testing of the sample.

18. The method according to claim 16, wherein the removably attached filtering element is configured for filtering a turbid sample by adhering the removably attached filtering element to the cover element along a periphery to be peelable from the multiplexed chemical testing strip device after performing a filtering operation of the turbid sample.

19. A multiplexed chemical testing strip device, comprising:

a hydrophobic paper-based strip housing element configured to receive a plurality of colorimetric testing strips;

one or more alignment markers arranged on the hydrophobic paper-based housing element for placement of the plurality of colorimetric testing strips;

a cover element arranged above the strip housing element and including a machine-readable test identifier comprising a Quick Response (QR) code, a barcode, or a Radio-Frequency Identification (RFID) on an upper surface;

a removably attached filtering element configured to remove contaminates that can change a shade of the one or more testing strips and arranged on the hydrophobic paper-based strip housing element to reduce a distortion of an image of the one or more testing strips; and a color reference information area on an upper surface of the cover element configured to provide a result interpretation and a digitalization by a digital Information Technology (IT) system, wherein at least one of the machine-readable test identifier or the color reference information identifies the test being performed.

20. The testing strip device according to claim 19, wherein the plurality of testing strips received by the hydrophobic paper-based strip housing element display colorimetric results, and at least some of the plurality of testing strips secured by the hydrophobic paper-based strip housing element are configured to perform different chemical testing of the sample, respectively.

* * * * *